United States Patent [19]

Suzuki et al.

[11] Patent Number: 5,182,284

[45] Date of Patent: Jan. 26, 1993

[54] PIPERAZINE COMPOUNDS, PROCESSES FOR PREPARATION THEREOF AND MEDICAL USES THEREOF

[75] Inventors: Masahiro Suzuki; Kenji Nozaki, both of Hannou; Makoto Kajitani, Irumagun; Mitsugi Yasumoto, Honjo; Naohiko Ono; Takashi Shindo, both of Tokushima, all of Japan

[73] Assignee: Taiho Pharmaceutical Co., Ltd., Tokyo, Japan

[21] Appl. No.: 761,974

[22] PCT Filed: Jan. 1, 1991

[86] PCT No.: PCT/JP91/00060

§ 371 Date: Sep. 25, 1991

§ 102(e) Date: Sep. 25, 1991

[87] PCT Pub. No.: WO91/11444

PCT Pub. Date: Aug. 8, 1991

[30] Foreign Application Priority Data

Jan. 26, 1990 [JP] Japan ................................. 2-16583

[51] Int. Cl.$^5$ ................ A61K 31/495; C07D 295/00; C07D 241/04
[52] U.S. Cl. ...................... 514/255; 514/252; 514/253; 544/357; 544/377; 544/382; 544/383; 544/386; 544/391; 544/399; 544/400
[58] Field of Search ............ 544/357, 377, 382, 383, 544/386, 391, 399, 400; 514/252, 253, 255

[56] References Cited

U.S. PATENT DOCUMENTS

| | | | |
|---|---|---|---|
| 4,123,530 | 10/1978 | Corvi-Mora | 544/400 |
| 4,252,804 | 2/1981 | Joullié et al. | 544/382 |
| 4,267,175 | 5/1981 | Watts | 544/382 |
| 4,278,796 | 7/1981 | Corvi-Mora | 564/400 |
| 4,981,853 | 1/1991 | Mueller et al. | 544/399 |
| 4,988,688 | 1/1991 | Kester et al. | 544/400 |
| 4,990,511 | 2/1991 | Nakajima et al. | 544/400 |

FOREIGN PATENT DOCUMENTS 111583 9/1977 Japan .
203060 12/1982 Japan .
22056 1/1986 Japan .

Primary Examiner—Cecilia Tsang
Attorney, Agent, or Firm—Nikaido, Marmelstein, Murray & Oram

[57] ABSTRACT

Disclosed are a piperazine compound of the formula below or a pharmaceutically acceptable salt thereof, medical uses thereof, and processes for preparing the same:

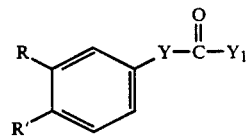

wherein each of R and R' is —OH, a lower alkoxy, a halo, H, a di(lower alkyl) hydrogenphosphate residue or a group —OR" (R" is an aralkyl group, etc.), etc., Y is —CH=CH— or —(CH$_2$)$_m$— (m is 0, 1 or 2), and Y$_1$ is a group of the formula

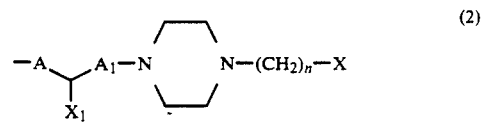

(2)

(wherein A is —NH— or —O—, A$_1$ is a methylene or a carbonyl, n is 6-20, X is —OH, H or a lower alkoxycarbonyl, and X$_1$ is an optionally halo-substituted phenyl or H) or a group of the formula

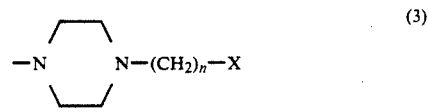

(3)

(wherein X and n are as defined above), provided that when Y$_1$ is the group of the formula (3), each of R and R' is an —OH group.

20 Claims, No Drawings

PIPERAZINE COMPOUNDS, PROCESSES FOR PREPARATION THEREOF AND MEDICAL USES THEREOF

TECHNICAL FIELD

The present invention relates to novel piperazine compounds having an activity of inhibiting lipoxygenase and an activity of inhibiting cyclooxygenase, or pharmaceutically acceptable salts thereof.

BACKGROUND ART

Leukotrienes produced from arachidonic acid by the action of 5-lipoxygenase, and prostaglandins produced therefrom by the action of cyclooxygenase are considered to eminently participate in the development of allergic asthma, allergic rhinitis, inflammations or the like. Consequently it is desired to inhibit both 5-lipoxygenase and cyclooxygenase in order to effectively and accurately suppress various allergic diseases, inflammations and the like. Thus the development of medicaments capable of potently inhibiting these enzymes is ardently desired.

DISCLOSURE OF THE INVENTION

The present inventors conducted extensive research in view of the foregoing problems in the background art, and found that novel piperazine compounds represented by the formula (I) below and salts thereof have a high lipoxygenase-inhibiting activity and a high cyclooxygenase-inhibiting activity and are useful as medicaments. The present invention has been accomplished based on this novel finding.

According to the present invention, there is provided a piperazine compound represented by the formula (1)

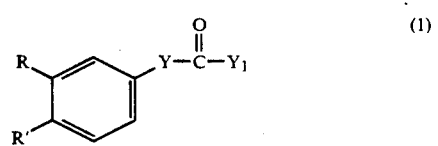

(1)

wherein R and R' are the same or different and each represents a hydroxy group, a lower alkoxy group, a halogen atom, a hydrogen atom, a di(lower alkyl) hydrogenphosphate residue or a group —OR" (wherein R" is an aralkyl group, a lower alkoxycarbonyl group, an amino acid residue, a lower alkylcarbonyl group or a lower alkylcarbamoyl group) or R and R' taken together form a methylenedioxy group, Y is —CH=CH— or —(CH)$_m$— (wherein m is 0, 1 or 2), and Y$_1$ is a group represented by the formula (2)

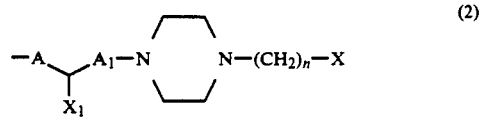

(2)

(wherein A is —NH— or —O—, A$_1$ is a methylene group or a carbonyl group, n is 6 to 20, preferably 6 to 15, X is a hydroxy group, a hydrogen atom or a lower alkoxycarbonyl group, and X$_1$ is a phenyl group which may be substituted with a halogen atom (especially 1, 2 or 3 halogen atoms) or a hydrogen atom), or a group represented by the formula (3)

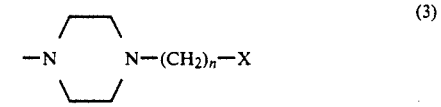

(3)

(wherein X and n are as defined above), provided that when Y is the group of the formula (3), each of R and R' is a hydroxy group; or a pharmaceutically acceptable salt thereof.

The compounds of the invention have a high lipoxygenase-inhibiting activity and a high cyclooxygenase-inhibiting activity. Examples of the lipoxygenase are 5-lipoxygenase, 12-lipoxygenase, 15-lipoxygenase, etc. The compounds of the invention exhibit a high activity of inhibiting especially 5-lipoxygenase.

The compounds of the invention have a high lipoxygenase inhibitory effect and a high cyclooxygenase inhibitory effect, and are useful as an anti-asthmatic agent, anti-allergic agent, agent for treating encephalopathy, cardiovascular agent, agent for treating nephritis, anti-inflammatory analgesic, anti-rheumatic agent, agent for treating dermatosis such as psoriasis and liver disease agent.

Accordingly the present invention provides an anti-asthmatic agent, anti-allergic agent, agent for treating encephalopathy, cardiovascular agent, agent for treating nephritis, anti-inflammatory analgesic, anti-rheumatic agent, agent for treating dermatosis such as psoriasis and liver disease agent, the agents each comprising an effective amount of the compound of the formula (1) or a pharmaceutically acceptable salt thereof, and a pharmaceutical carrier.

According to the invention, there are also provided methods of treating asthma, allergy, encephalopathy, diseases of circulatory organs, nephritis, inflammations, rheumatism, dermatosis such as psoriasis and liver diseases, the methods each comprising administering to patients an effective amount of the compound of the formula (1) or a pharmaceutically acceptable salt thereof.

Examples of lower alkoxy groups represented by R and R, in the present invention are straight- or branched-chain alkoxy groups having 1 to 4 carbon atoms, such as methoxy, ethoxy, n-propoxy, isopropoxy, n-butoxy, isobutoxy, secbutoxy, t-butoxy, etc. Examples of di(lower alkyl) hydrogenphosphate residues are residues of phosphoric acid substituted with 2 alkyl groups having 1 to 4 carbon atoms, such as dimethyl phosphate, diethyl phosphate, dipropyl phosphate, dibutyl phosphate, etc., especially a group represented by the formula —O—P(O)(OR$^0$)$_2$ wherein R$^0$ is an alkyl group having 1 to 4 carbon atoms.

Examples of halogen atoms represented by R and R' and halogen atoms as substituents for the phenyl group represented by X$_1$ are fluorine, chlorine, bromine, iodine, etc.

With respect to the groups represented by R", aralkyl groups include alkyl groups having 1 to 6 carbon atoms and substituted with a phenyl group, such as benzyl, phenethyl, phenylpropyl, etc., and lower alkoxycarbonyl groups include straight- or branched-chain alkoxycarbonyl groups having 2 to 5 carbon atoms, such as methoxycarbonyl, ethoxycarbonyl, n-propoxycarbonyl, isopropoxycarbonyl, n-butoxycarbonyl, isobutoxycarbonyl, sec-butoxycarbonyl, t-butoxycarbonyl, etc. The amino acid residue means a group formed by removing the hydroxy group from the carboxyl group of amino acid. Examples of amino acids are glycine, alanine, methionine, valine, serine, proline, leucine, isoleucine, glutamine, histidine, phenylalanine, phenylglycine and like natural or synthetic amino acids, and N-protected amino acids with the amino group protected with $C_1$-$C_6$ lower alkyl group, $C_2$-$C_5$ lower acyl group, $C_2$-$C_5$ lower alkoxycarbonyl group, benzyloxycarbonyl group or the like, such as N,N-dimethylglycine, N-acetylglycine, N-t-butoxycarbonylglycine, N-benzyloxycarbonylglycine, N-acetylvaline, N-t-butoxycarbonylvaline, etc. Examples of lower alkylcarbonyl groups are straight- or branched-chain alkylcarbonyl groups having 2 to 5 carbon atoms, such as methylcarbonyl, ethylcarbonyl, n-propylcarbonyl, isopropylcarbonyl, n-butylcarbonyl, isobutylcarbonyl, sec-butylcarbonyl, t-butylcarbonyl, etc. Examples of lower alkylcarbamoyl groups are carbamoyl groups mono- or di-substituted with lower alkyl groups having 1 to 4 carbon atoms, such as methylcarbamoyl, dimethylcarbamoyl ethylcarbamoyl, diethylcarbamoyl, propylcarbamoyl, dipropylcarbamoyl, isopropylcarbamoyl, diisopropylcarbamoyl, butylcarbamoyl, dibutylcarbamoyl, etc.

Examples of lower alkoxycarbonyl groups represented by X are straight- or branched-chain alkoxycarbonyl groups having 2 to 5 carbon atoms which are exemplified above for the group R".

Pharmaceutically acceptable salts of the piperazine compounds of the invention include, for example, salts thereof produced using an inorganic acid such as hydrochloric acid, sulfuric acid, phosphoric acid or the like or an organic acid such as maleic acid, succinic acid, malic acid, oxalic acid, fumaric acid or the like.

In the compounds of the formula (1), preferably R and R' are the same or different and each represents a hydroxy group, a lower alkoxy group, a hydrogen atom, a di(lower alkyl) hydrogenphosphate residue or a group —OR" (wherein R" is a lower alkoxycarbonyl group or an amino acid residue), more preferably R and R' are the same or different and each represents a hydroxy group, a lower alkoxy group or a group —OR" (wherein R" is a lower alkoxycarbonyl group).

Preferred Y groups include —CH=CH—. Preferred $Y_1$ groups include the groups of the formula (2). Of the groups of the formula (2), preferred are those wherein A is —NH—, A is a methylene group or a carbonyl group, n is 6 to 15, X is a hydroxy group or a hydrogen atom and $X_1$ is a phenyl group or a hydrogen atom, and particularly those wherein A is —NH—, $A_1$ is a methylene group or a carbonyl group, n is 8 to 12, X is a hydrogen atom and $X_1$ is a phenyl group or a hydrogen atom.

Of the compounds of the formula (1), preferred are those wherein R and R' are the same or different and each represents a hydroxy group, a lower alkoxy group, a hydrogen atom, a di(lower alkyl) hydrogenphosphate residue or a group —OR" (wherein R" is a lower alkoxycarbonyl group or an amino acid residue), Y is —CH=CH— and $Y_1$ is a group of the formula (2) wherein A is —NH—, $A_1$ is a methylene group or a carbonyl group, n is 6 to 15, X is a hydroxy group or a hydrogen atom and X is a phenyl group or a hydrogen atom.

Most preferred compounds are those wherein R and R' are the same or different and each represents a hydroxy group, a lower alkoxy group, or a group —OR" (wherein R" is a lower alkoxycarbonyl group, Y is —CH=CH— and $Y_1$ is a group of the formula (2) wherein A is —NH—, $A_1$ is a methylene group or a carbonyl group, n is 8 to 12, X is a hydrogen atom and $X_1$ is a phenyl group or a hydrogen atom.

The compounds of the formula (1) according to the invention can be prepared by the processes illustrated below in Reaction Schemes (i) to (iii).

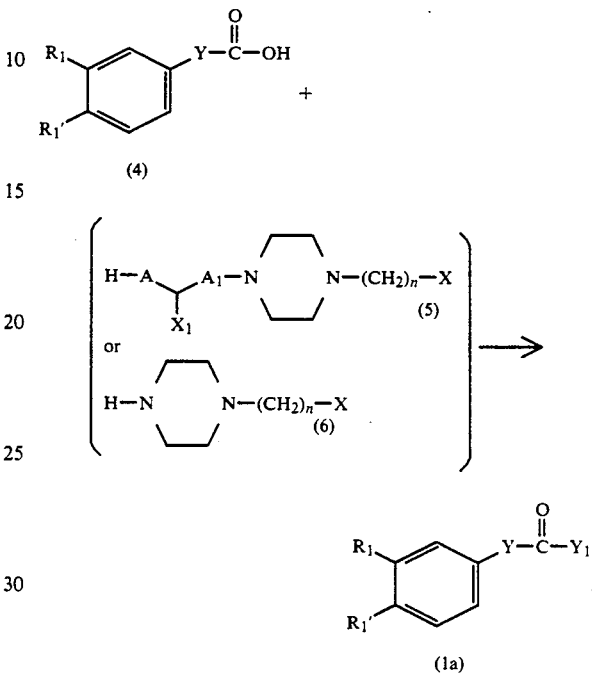

In the foregoing formulae, Y, $Y_1$, A, $A_1$, X, $X_1$ and n are as defined above; $R_1$ and $R_1'$ are the same or different and each represents a hydroxy group, a lower alkoxy group, an aralkyloxy group, a halogen atom or a hydrogen atom, or $R_1$ and $R_1'$ taken together form a methylenedioxy group.

The desired piperazine compound of the formula (1a) is prepared by reacting a carboxylic acid of the formula (4) with an alcohol or an amine of the formula (5) or an amine of the formula (6) in a solvent in the presence of a base using a condensing agent. If the groups $R_1$ and/or $R_1'$ in the formula (4) or the group X in the formula (5) or (6) is (are) a hydroxy group, condensation may be conducted after protecting the group with a suitable protective group. Useful protective groups are not specifically limited insofar as the protective groups used do not adversely affect others when said protective group is removed by deprotection. Examples of protective groups are methoxyethoxymethyl, methoxymethyl, tetrahydrofuranyl, tetrahydropyranyl, etc. These protective groups can be introduced by the method disclosed in Journal of American Chemical Society, 100, 8031 (1978). Solvents useful in the reaction are not specifically limited insofar as they do not participate in the reaction. Useful solvents include, for example, ether, tetrahydrofuran and like ethers, methylene chloride, chloroform and like halogenated hydrocarbons, benzene, toluene and like aromatic hydrocarbons, N,N-dimethylformamide, dimethylsulfoxide and like aprotic polar solvents, etc. Useful condensing agents include, for example, N,N-dicyclohexylcarbodiimide, ethoxycarbonyl chloride, etc. Useful bases include, for example, 4-dimethylaminopyridine, 1-hydroxybenzotriazole, pyridine, triethylamine, etc. In the reaction, it is preferable to use, per equivalent of the compound of the formula (4), about 1 to about 2 equivalents of the compound of the formula (5) or (6), about 1 to about 2 equivalents of the condensing agent and a catalytic amount or about 1 to about 2 equivalents of the base. The reaction time is about 4 to about 48 hours. The reaction advantageously proceeds if conducted at a temperature between ice cooling temperature and room temperature.

The compounds of the formula (4) are all known compounds. The compounds of the formulae (5) and (6) can be prepared by conventional processes or by the process illustrated later in Reaction Scheme (iv) and Reference Examples 1 to 11.

The compounds of the formula (1) wherein at least one of R and R' is (are) a di(lower alkyl) hydrogenphosphate residue or a group —OR" wherein R" is a lower alkoxycarbonyl group, an amino acid residue, a lower alkylcarbonyl group or a lower alkylcarbamoyl group can be prepared preferably by the processes illustrated below in Reaction Schemes (ii) and (iii) which, however, are not specifically limitative. Other processes can be employed without specific limitation insofar as an O-acylation reaction is effected.

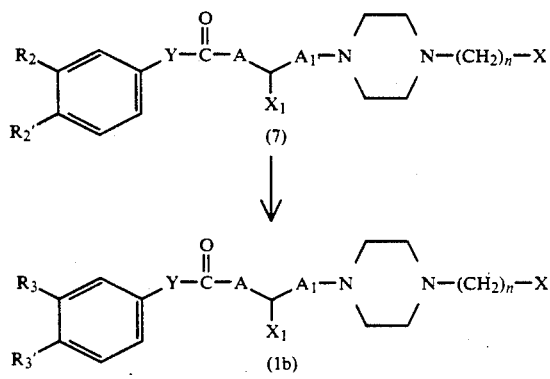

In the foregoing formulae, Y, A, $A_1$, X, $X_1$ and n are as defined above; $R_2$ and $R_2'$ are the same or different and each represents a hydroxy group, a lower alkoxy group, a halogen atom or a hydrogen atom with the proviso that at least one of $R_2$ and $R_2'$ is (are) a hydroxy group; and $R_3$ and $R_3'$ are the same or different and each represents a lower alkoxy group, is a lower alkylcarbonyl group or an amino acid residue) with the proviso that at least one of $R_3$ and $R_3'$ is (are) said —$OR_3''$ group.

The desired piperazine compound of the formula (1b) is prepared by reacting the compound of the formula (7) obtained according to Reaction Scheme (i) with a lower fatty acid or its acid chloride or an amino acid or an N-protected amino acid in a suitable solvent in the presence of a condensing agent. Useful lower fatty acids include, for example, straight- or branched-chain lower fatty acids having 2 to 5 carbon atoms, such as acetic acid, propionic acid, butyric acid, isobutyric acid, valeric acid, isovaleric acid, pivalic acid, etc. Their acid chlorides include acid chlorides of straight- or branched-chain lower fatty acids having 2 to 5 carbon atoms, such as acetyl chloride, propionyl chloride, butyryl chloride, isobutyryl chloride, valeryl chloride, isovaleryl chloride, pivaloyl chloride, etc. Examples of amino acids include those exemplified above for the R" group, such as glycine, alanine, valine, methionine, serine, proline, leucine, isoleucine, glutamine, histidine, phenylalanine, Usually preferred is the foregoing N-protected amino acid with the amino group protected. Useful solvents are not specifically limited insofar as they do not participate in the reaction. Examples of the solvents are ether, tetrahydrofuran and like ethers, methylene chloride, chloroform and like halogenated hydrocarbons, benzene, toluene and like aromatic hydrocarbons, N,N-phenylglycine dimethylformamide, dimethylsulfoxide and like aprotic polar solvents, etc. When a lower fatty acid or N-protected amino acid is used, useful condensing agents include those usually used in the synthesis of peptides, such as N,N-dicyclohexylcarbodiimide, ethoxycarbonyl chloride, etc. In this case, an additive may be used when so required. When an organic amine such as N,N-dimethylaminopyridine, 1-hydroxybenzotriazole or the like is used as an additive, the reaction may advantageously proceed. In the reaction using a lower fatty acid chloride, a base can generally be used as the condensing agent. Useful bases are, for example, pyridine, triethylamine and like organic bases, sodium hydrogencarbonate, potassium hydrogencarbonate, sodium carbonate, potassium carbonate and like inorganic bases, etc. As to the proportions of starting materials for the reaction, it is preferable to use, per equivalent of the compound of the formula (7), about to about 2.5 equivalents of the lower fatty acid or acid chloride thereof or N-protected amino acid and about 1 to about 2.5 equivalents of the condensing agent. If an organic amine is used as the additive, about 1 to about 2.5 equivalents thereof is used per equivalent of the compound of the formula (7). The reaction time is about 1 to about 15 hours, and the reaction temperature is between ice cooling temperature and room temperature. When a N-protected amino acid is used, the protective group may be removed, when required, in a conventional manner. Useful agents for removing the protective group are those conventionally used, such as hydrochloric acid, sulfuric acid and like inorganic acids, and p-toluenesulfonic acid, trifluoroacetic acid, formic acid and like organic acids. The conditions for the deprotection may be the same as those already known or conventionally employed in the synthesis of peptides.

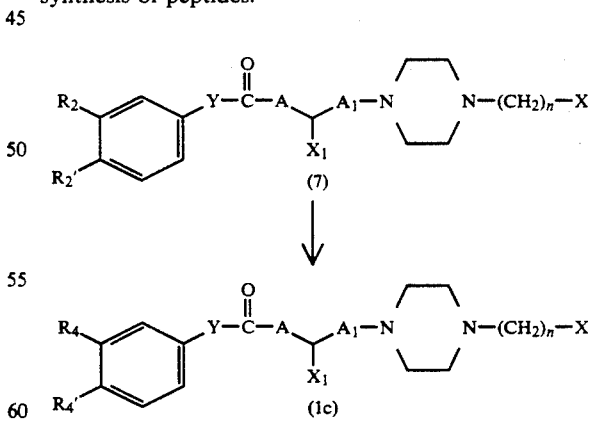

In the foregoing formulae, Y, A, $A_1$, X, $X_1$ and n are as defined above; $R_2$ and $R_2'$ are the same or different and each represents a hydroxy group, a lower alkoxy group, a halogen atom or a hydrogen atom with the proviso that at least one of $R_2$ and $R_2'$ is (are) a hydroxy group; and $R_4$ and $R_4'$ are the same or different and each represents a lower alkoxy group, a halogen atom, a hydrogen atom, di(lower alkyl) hydrogenphosphate residue or a group —OR$_4''$ (wherein R$_4''$ is a lower alkylcarbamoyl group or a lower alkoxycarbonyl group) with the proviso that at least one of R$_4$ and R$_4'$ is (are) said di(lower alkyl) hydrogenphosphate residue or —OR$_4''$ group.

The desired piperazine compound of the formula (1c) is prepared by reacting the compound (7) obtained according to Reaction Scheme (i) with a lower alkyl isocyanate, di(lower alkyl) chlorophosphate or lower alkoxycarbonyl chloride (lower alkyl chlorocarbonate) in a suitable solvent in the presence of a base. Examples of lower alkyl isocyanates are straight- or branched-chain (C$_1$-C$_4$ lower alkyl) isocyanates, such as methyl isocyanate, ethyl isocyanate, n-propyl isocyanate, isopropyl isocyanate, n-butyl isocyanate, isobutyl isocyanate, sec-butyl isocyanate, t-butyl isocyanate, etc. Examples of di(lower alkyl) chlorophosphates are di(C$_1$-C$_4$ alkyl) chlorophosphates, such as dimethylchlorophosphate, diethylchlorophosphate, dipropylchlorophosphate, dibutylchlorophosphate, etc. Examples of lower alkoxycarbonyl chlorides are C$_2$-C$_5$ alkoxycarbonyl chlorides such as methoxycarbonyl chloride, ethoxycarbonyl chloride, n-propoxycarbonyl chloride, isopropoxycarbonyl chloride, n-butoxycarbonyl chloride, isobutoxycarbonyl chloride, sec-butoxycarbonyl chloride, t-butoxycarbonyl chloride, etc. Solvents useful in the reaction are not specifically limited insofar as they do not participate in the reaction. Useful solvents include those which are usable in Reaction Scheme (ii) and amines such as pyridines. Useful bases include triethylamine, pyridine, etc. As to the proportions of starting materials for the reaction, the reaction advantageously proceeds if the lower alkyl isocyanate, di(lower alkyl) chlorophosphate or lower alkoxycarbonyl chloride and the base are used respectively in amounts of about 2 to about 3 equivalents per equivalent of the compound of the formula (7). The reaction time is about 1 to about 15 hours, and the reaction temperature is between ice cooling temperature and room temperature.

Of the desired piperazine compounds of the formula (1c), those wherein R$_4''$ is a lower alkylcarbamoyl group or a lower alkoxycarbonyl group can be prepared by another process. The process comprises reacting the compound of the formula (7) with phosgene or N,N'-carbonyldiimidazole in a suitable solvent, and reacting the resulting reaction product with mono or di(lower alkyl) amine or lower alcohol in the presence of a base if required. The phosgene or N,N'-carbonyldiimidazole is usually used in an amount of about 1 to about 2.5 moles per mole of the compound of the formula (7). Solvents useful in the reaction are not specifically limited insofar as they do not participate in the reaction. Useful solvents include ether, tetrahydrofuran and like ethers, methylene chloride, chloroform and like halogenated hydrocarbons, benzene, toluene and like aromatic hydrocarbons, etc. The reaction temperature is between ice cooling temperature and room temperature. The reaction time is about 0.5 to about 1 hour. With respect to the subsequent reaction, examples of mono or di(-lower alkyl) amines are straight- or branched-chain mono or di(C$_1$-C$_4$ alkyl)amines such as methylamine, dimethylamine, ethylamine, diethylamine, n-propylamine, dipropylamine, isopropylamine, diisopropylamine, butylamine, dibutylamine, etc. Examples of useful lower alcohols are C$_1$-C$_4$ alcohols such as methanol, ethanol, propanol, isopropanol, n-butanol, isobutanol, sec-butanol and t-butanol, etc. Examples of useful bases are organic bases such as triethylamine, pyridine, etc. and inorganic bases such as sodium hydrogencarbonate, potassium hydrogencarbonate, sodium carbonate, potassium carbonate, etc. The same solvents as exemplified above can be used in the process. As to the proportions of starting materials for the reaction, the reaction advantageously proceeds if lower alkylamine or lower alcohol and the base are used respectively in amounts of about 2 to about 4 equivalents per equivalent of the compound prepared by reacting the compound of the formula (7) with phosgene or N,N'-carbonylimidazole. The reaction temperature is between ice cooling temperature and room temperature. The reaction is completed in about 1 to about 24 hours.

Of the compounds of the formula (5), those wherein A is —O— can be prepared by the process disclosed, for example, in Japanese Unexamined Patent Publication No.152656/1986.

The compounds wherein A is —NH— can be prepared, for example, according to Reaction Scheme (iv) below.

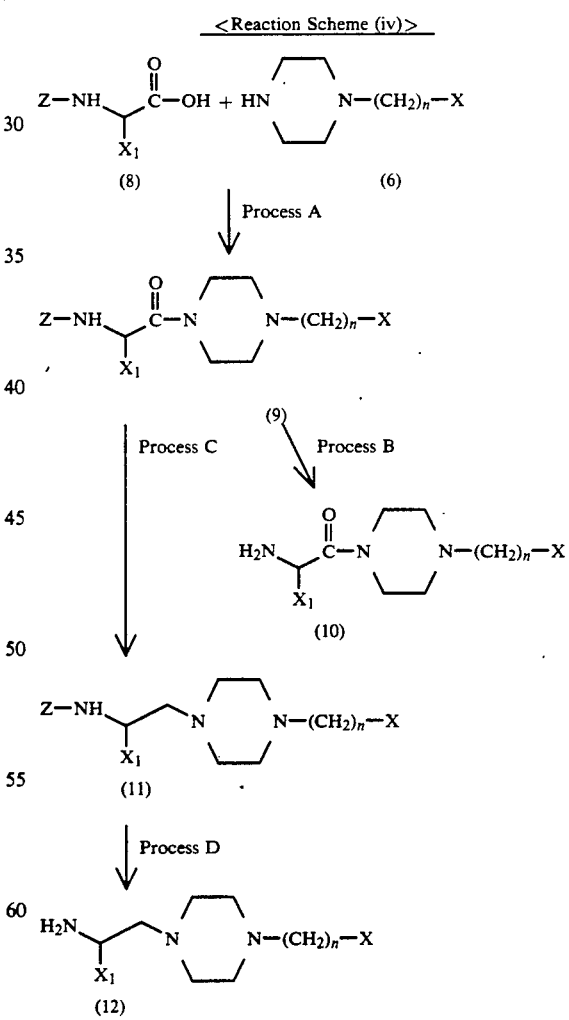

In the foregoing formulae, Z is a t-butoxycarbonyl group or a benzyloxycarbonyl group, and X, X$_1$ and n are as defined above.

Process A

The carboxylic acid of the formula (8) is reacted with the amine of the formula (6) in a solvent in the presence of a base using a condensing agent, whereby the piperazine compound of the formula (9) is produced. Useful solvents are not specifically limited insofar as they do not participate in the reaction. Examples of solvents are ether, tetrahydrofuran and like ethers, methylene chloride, chloroform and like halogenated hydrocarbons, benzene, toluene and like aromatic hydrocarbons, N,N-dimethylformamide, dimethylsulfoxide and like aprotic polar solvents, etc. Useful condensing agents are not specifically limited insofar as they are those conventionally used in the synthesis of peptides, such as N,N-dicyclohexylcarbodiimide, ethoxycarbonyl chloride, etc. Useful bases include, for example, 4-dimethylaminopyridine, 1-hydroxybenzotriazole, etc. As to the proportions of starting materials for the reaction, it is preferred to use, per equivalent of the compound of the formula (8), 1 to 2 equivalents of the compound of the formula (6), 1 to 2 equivalents of the condensing agent and a catalytic amount or 1 to 2 equivalents of the base. The reaction time is about 1 to about 48 hours. The reaction advantageously proceeds if conducted at a temperature between ice cooling temperature and room temperature.

Process B

The compound of the formula (9) is treated with an acid or hydrogenated in a solvent to remove the group Z, whereby the piperazine compound of the formula (10) is produced. Solvents useful in the reaction are not specifically limited insofar as they do not participate in the reaction. Useful solvents include the solvents exemplified above for use in (Process A), and methanol, ethanol and like protonic polar solvents. Useful acids are not specifically limited insofar as they are those commonly employed in removing the protective groups of amino group. Examples of useful acids are hydrochloric acid, sulfuric acid, trifluoroacetic acid, hydrobromic acid, etc. If hydrogenation is effected to remove the protective group, use of a catalyst such as palladium carbon or the like enables the reaction to advantageously proceed. The conditions for the deprotection may be those already known or conventionally employed, for example, in removing the protective groups in the synthesis of peptides.

Process C

The compound of the formula (9) is reacted with a reducing agent in a solvent, whereby the piperazine compound of the formula (11) is produced. Useful solvents are not specifically limited insofar as they do not participate in the reaction. For example, the solvents exemplified above for use in (Process A) can be used. The reaction time is about 2 to about 48 hours, and the reaction is conducted with ice cooling. Useful reducing agents include lithium aluminum hydride, aluminum hydride, etc. Such reducing agent is usually used in an amount of about 2 to about 10 equivalents per equivalent of the compound of the formula (9).

Process D The compound of the formula (11) is reacted in the same manner as in (Process B), whereby the piperazine compound of the formula (12) is produced.

Reference Examples to be described later specifically illustrate the preparation of compounds by (Processes A to D).

The compounds of the invention prepared by the foregoing reactions can be converted into salts thereof by a conventional method as by being reacted with the foregoing organic or inorganic acid in a solvent such as ethers, lower alcohols, ethyl acetate, hexane or the like at approximately room temperature.

The compounds obtained in Reaction Schemes (i) to (iv) can be isolated and purified by usual means conventionally employed in the art such as concentration, filtration, recrystallization, various types of chromatography, etc.

For use as medicaments, the compounds of the present invention can be made into various pharmaceutical dosage forms according to prophylactic or therapeutic purpose. Examples of pharmaceutical dosage forms are oral preparations, injections, suppositories and so on. Such preparations can be formulated in a manner already known or conventional by those skilled in the art.

For the formulation of solid preparations for oral administration, an excipient and, when required, a binder, disintegrator, lubricant, coloring agent, corrigent, flavor, etc. are added to the compound of the invention, and then a preparation is formulated in a usual manner as tablets, 15 coated tablets, granules, powders, capsules or the like. Such additives are those already known in the art, and useful examples are excipients such as lactose, sucrose, sodium chloride, glucose, starch, calcium carbonate, kaolin, microcrystalline cellulose and silicic acid; binders such as water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate and polyvinyl pyrrolidone; disintegrators such as dried starch, sodium alginate, agar powder, sodium hydrogencarbonate, calcium carbonate, sodium lauryl sulfate, stearic acid monoglyceride and lactose; lubricants such as purified talc, stearic acid salt, borax and polyethylene glycol; corrigents such as sucrose, bitter orange peel, citric acid and tartaric acid, etc.

For the formulation of liquid preparations for oral administration, a corrigent, buffer, stabilizer, flavor, etc. can be added to the compound of the present invention, and the mixture can be formulated in a usual manner into an oral liquid preparations, syrup, elixir or the like. Examples of useful corrigents are those exemplified above. Examples of buffers are sodium citrate, etc. Examples of stabilizers are tragacanth, gum arabic, gelatin, etc.

Injections can be prepared as a subcutaneous injection, intramuscular injection, intravenous injection in a conventional manner by adding to the compound of the invention a pH adjusting agent, buffer, stabilizer, isotonic agent, local anesthetic, etc. Examples of pH adjusting agents and buffers are sodium citrate, sodium acetate, sodium phosphate, etc. Examples of stabilizers are sodium pyrosulfite, EDTA, thioglycolic acid, thiolactic acid, etc. Examples of local anesthetics are procaine hydrochloride, lidocaine hydrochloride, etc.

Suppositories can be prepared in a usual manner by adding to the compound of the invention a pharmaceutically acceptable carrier already known in the art, such as polyethylene glycol, lanolin, cacao fat and oil, fatty acid triglyceride and, if required, a surfactant, e.g. Tween (registered trademark).

The amount of the compound of the present invention to be incorporated into each of the administration units varies with the symptoms of the patient or with the type of the preparation. Preferably the amount per administration unit is about 1 to about 1,000 mg for oral preparations, about 0.1 to about 500 mg for injections, or about 5 to about 1,000 mg for suppositories. The dosage per day of the drug in the above dosage forms is variable with the symptoms, body weight, age, sex and other factors of the patient, but usually ranges from about 0.1 to about 5,000 mg, preferably from about 1 to about 1,000 mg for human adult. The preparation is preferably administered in a single dose or in two to four divided doses.

EXAMPLES

The present invention will be described below in more detail with reference to the following Reference Examples and Examples.

Reference Example 1

Synthesis of 1-(2-amino-2-phenylacetyl)-4-decylpiperazine

A 20 g (0.18 mole) quantity of N-formylpiperazine, 37.2 ml (0.18 mole) of 1-bromodecane and 25 g (0.18 mole) of potassium carbonate were suspended in 20 ml of N,N-dimethylformamide and the suspension was stirred at 80° C. for 3 hours. The suspension was further extracted with 300 ml of benzene, and the organic layer was washed with water, dried over anhydrous magnesium sulfate and concentrated under reduced pressure. The residue was dissolved in 80 ml of methanol, and 20 ml of concentrated hydrochloric acid was added thereto and the mixture was refluxed for 3 hours. The solvent was evaporated under reduced pressure and the precipitated crystals were washed with acetone, giving 35.6 g (yield: 66%) of N-decylpiperazine as the hydrochloride.

A 2.3 g (8.64 mmoles) quantity of N,N,-dicyclohexylcarbodiimide was added to 20 ml of a solution of 2.0 g (7.35 mmoles) of N-decylpiperazine, 1.9 g (7.56 mmoles) of N-t-butoxycarbonylphenylglycine, 1.3 g (15.5 mmoles) of sodium hydrogen carbonate and 122 mg (1.0 mmole) of 4-dimethylaminopyridine in anhydrous methylene chloride. The mixture was stirred at room temperature for 12 hours. The precipitated crystals were collected by filtration and washed with methylene chloride. Mother liquor and the washings were concentrated under reduced pressure and the residue was purified by silica gel column chromatography (chloroform:methanol=15:1), giving 2.8 g (yield: 83%) of 1-(N-t-butoxycarbonylphenylglycyl)-4-decylpiperazine.

$^1$H-NMR (CDCl$_3$) δ ppm: 0.87 (3H, m), 1.24–1.41 (25H, m), 2.14–2.39 (6H, m), 3.30–3.68 (4H, m), 5.55 (1H, d, J=7.1 Hz), 6.12 (1H, d, J=7.1 Hz), 7.23–7.33 (5H, m). MS: 460 (M+1).

A 2.9 g (6.32 mmoles) quantity of 1-(N-t-butoxycarbonylphenylglicyl)-4-decylpiperazine was dissolved in 5 ml of ethyl acetate, and 20 ml of 4N hydrochloric acid-ethyl acetate solution was added thereto with ice-cooling and the mixture was stirred for 1 hour. The precipitated crystals were collected by filtration, washed with a small quantity of ether and dried under reduced pressure, giving 2.5 g (yield: 90%) of 1-(2-amino-2-phenylacetyl)-4-decylpiperazine as the hydrochloride.

$^1$H-NMR (DMSO - d$_6$+D$_2$O) δ ppm: 0.86 (3H, m), 1.27 (12H, m), 1.76 (2H, m), 3.11–3.54 (12H, m), 1.72 (1H, m), 7.10–7.57 (5H, m).

MS: 358 (M-1).

Reference Example 2

Synthesis of 1-(2-aminoacetyl)-4-decylpiperazine

The same procedure as in Reference Example 1 was repeated with the exception of using N-t-butoxycarbonylglycine in place of N-t-butoxycarbonylphenylglycine, giving 1-(2-aminoacetyl)-4-decylpiperazine as the hydrochloride in a yield of 76%.

$^1$H-NMR (DMSO - d$_6$+D$_2$O) δ ppm: 0.86 (3H, m), 1.26 (12H, m), 1.72 (2H, m), 3.09–4.52 (14H,m).

MS: 283 (M+).

Reference Example 3

Synthesis of 1-(2-amino-2-phenylethyl)-4-decylpiperazine

A solution of 17 g (37 mmoles) of 1-(N-t-butoxycarbonylphenylglycyl)-4-decylpiperadine obtained in the same manner as in Reference Example 1 in 50 ml of tetrahydrofuran was added dropwise with ice-cooling to 140 ml of a solution of aluminum hydride in terahydrofuran [Journal of American Chemical Society., 90, 2927 (1968)], and the mixture was stirred for 3 hours. To the solution thus obtained was added dropwise a solution of 2.1 g of potassium hydroxide in 7.6 ml of water, and the mixture was stirred at room temperature for 12 hours. The precipitate was collected by filtration and washed with 100 ml of tetrahydrofuran. The mother liquor and the washings were combined and concentrated under reduced pressure. The residue was dissolved in 150 ml of ethyl acetate and the solution was washed sequentially with 80 ml of 0.5 N hydrochloric acid, an aqueous solution of saturated sodium hydrogen carbonate and a brine. The resulting solution was dried over anhydrous magnesium sulfate and concentrated under reduced pressure. The residue was treated in the same manner as in Reference Example 1, giving 9.9 g (yield: 59%) of 1-(2-amino-2-phenylethyl)-4-decylpiperazine as the hydrochloride. $^1$H-NMR (DMSO - d$_6$+D$_2$O) δ ppm: 0.86 (3H, m), 1.26 (12H, m), 1.70 (2H, m), 2.98–3.86 (14H, m), 4.72 (1H, m), 7.40–7.63 (5H, m).

MS: 344(M-1).

Reference Example 4

Synthesis of 1-(2-amino-2-phenylethyl)-4-dodecylpiperazine 1-(N-t-Butoxycarbonylphenylglycyl)-4-dodecylpiperazine obtained by following the general procedure of Reference Example 1 was treated in the same manner as in Reference Example 3, giving 1-(2-amino-2-phenylethyl)-4-dodecylpiperazine as the hydrochloride in a yield of 63%.

$^1$H-NMR (DMSO - d$_6$+D$_2$O) δ ppm: 0.86 (3H, m), 1.25 (18H, m), 1.70 (2H, m), 3.11–3.90 (12H, m), 4.76 (1H, m), 7.40–7.73 (5H, m).

MS: 374(M-1).

Reference Example 5

Synthesis of
1-(2-amino-2-phenylethyl)-4-pentadecylpiperazine 1-(N-t-Butoxycarbonylphenylglycyl)-4-pentadecylpiperazine obtained by following the general procedure of Reference Example 1 was treated in the same manner as in Reference Example 3, giving 1-(2-amino-2-phenylethyl)-4-pentadecylpiperazine as the hydrochloride in a yield of 60%.

$^1$H-NMR (DMSO - $d_6$+$D_2O$) δ ppm: 0.85 (3H, m), 1.24 (24H, m), 1.71 (2H, m), 3.10–3.75 (12H, m), 4.76 (1H, m), 7.33–7.62 (5H, m).
MS: 111(M-1).

Reference Example 6

Synthesis of 1-(2-aminoethyl)-4-decylpiperazine 1-(N-t-Butoxycarbonylglycyl)-4-decylpiperazine obtained as an intermediate in Reference Example 2 was treated in the same manner as in Reference Example 3, giving 1-(2-aminoethyl)-4-decylpiperazine as the hydrochloride in a yield of 65%.

$^1$H-NMR (DMSO - $d_6$+$D_2O$) δ ppm: 0.84 (3H, m), 1.27 (14H, m), 1.74 (2H, m), 3.15–3.51 (14H, m).
MS: 269(M+).

Reference Example 7

Synthesis of
1-(2-amino-2-phenylethyl)-4-octylpiperazine 1-(N-t-Butoxycarbonylphenylglycyl)-4-octylpiperazine obtained by following the general procedure of Reference Example 1 was treated in the same manner as in Reference Example 3, giving 1-(2-amino-2-phenylethyl)-4-octylpiperazine as the hydrochloride in a yield of 52%.

$^1$H-NMR (DMSO - $d_6$+$D_2O$) δ ppm: 0.86 (3H, m), 1.24 (12H, m), 2.13–2.71 (12H, m, +DMSO), 4.06 (1H, m), 7.23–7.40 (5H, m).
MS: 318(M+1), 211(M-106).

Reference Example 8

Synthesis of
1-(2-amino-2-phenylethyl)-4-hexylpiperazine 1-(N-t-Butoxycarbonylphenylglycyl)-4-hexylpiperazine obtained by following the general procedure of Reference Example 1 was treated in the same manner as in Reference Example 3, giving 1-(2-amino-2-phenylethyl)-4-hexylpiperazine as the hydrochloride in a yield of 61%.

$^1$H-NMR (DMSO - $d_6$+$D_2O$) δ ppm: 0.88 (3H, m), 1.29 (8H, m), 2.36–2.93 (12H, m, +DMSO), 4.18 (1H, m), 7.26–7.41 (5H, m).
MS: 183(M-106).

Reference Example 9

Synthesis of
1-(2-amino-2-phenylethyl)-4-[10-(2-tetrahydropyranyloxy)decyl]piperazine A 583 mg (1.40 mmoles) quantity of 1-benzyl-4-[10-(2-tetrahydropyranyloxy)decyl]piperazine was dissolved in 20 ml of ethanol, and 200 mg of 10% palladium-carbon was added thereto and the mixture was shaken at 3 atm. for 8 hours under a hydrogen atmosphere. The catalyst was filtered off and the filtrate was evaporated to dryness, giving 375 mg (yield: 82%) of N-[10-(2-tetrahydropyranyloxy)decyl]piperazine.
Then, using N-t-butoxycarbonylphenylglycine and N-[10-(2-tetrahydropyranyloxy)decyl]piperazine, 1-(2-amino-2-phenylacetyl)-4-[10-(2-tetrahydropyranyloxy)decyl]piperazine was prepared in the same manner as in Reference Example 1. The obtained product was treated by the same procedure as in Reference Example 3, giving 384 mg (yield: 75%) of 1-(2-amino-2-phenylethyl) -4-[10-(2tetrahydropyranyloxy)decyl]piperazine.

$^1$H-NMR (CDCl$_3$+$D_2O$) δ ppm: 1.28–1.63 (20H, m), 2.19–2.68 (14H, m), 3.25–3.86 (5H, m), 4.56 (1H, m), 7.24–7.38 (5H, m). MS: 444(M-1), 428(M-17).

Reference Example 10

Synthesis of 11-(1-piperazyl)undecanoic acid methyl ester

A 26.5 g (0.1 mole) quantity of 11-bromoundecanoic acid was dissolved in 300 ml of methanol, and 5 to 6 drops of sulfuric acid was added thereto and the mixture was stirred at room temperature for 24 hours and concentrated. A 500 ml quantity of ethyl acetate was added to the residue and the mixture was washed sequentially with 100 ml of water and 100 ml of a brine, followed by drying over anhydrous magnesium sulfate. Ethyl acetate was evaporated under reduced pressure and the residue was dissolved in 200 ml of dimethylformamide. To the solution were added 11.4 g (0.1 mole) of formylpiperazine and 18.5 g (0.22 mole) of sodium hydrogen carbonate. The mixture was stirred at 80° C. for 3 hours and concentrated under reduced pressure. A 500 ml quantity of ethyl acetate was added to the residue and the mixture was washed sequentially with 100 ml of water and 100 ml of a brine, followed by drying over anhydrous magnesium sulfate. Ethyl acetate was evaporated under reduced pressure. To the residue were added 300 ml of methanol and 50 ml of concentrated hydrochloric acid, and the mixture obtained was refluxed for 3 hours. The solvent was evaporated under reduced pressure and the precipitated white crystals were washed with acetone, giving 25 g (yield: 70%) of 11-(1-piperazyl)undecanoic acid methyl ester as the hydrochloride.

$^1$H-NMR (DMSO - $d_6$+$D_2O$) δ ppm: 1.0–1.94 (18H, m), 2.54 (2H, m), 3.14 (2H, m), 3.47 (6H, 3.57 (3H, s).
MS: 284(M+).

Reference Example 11

Synthesis of
1-(2-aminoacetyl)-4-(10-methoxycarbonyldecyl)piperazine

The 11-(1-piperazyl)undecanoic acid methyl ester hydrochloride obtained in Reference Example 10 and N-t-butoxycarbonylglycine were treated in the same manner as in Reference Example I, giving 1-(2-aminoacetyl)-4-(10-methoxycarbonyldecyl)piperazine in a yield of 69%.

$^1$H-NMR (DMSO - $d_6$+$D_2O$) δ ppm: 1.13–1.93 (20H, m), 2.99–3.30 (8H, m), 3.58 (3H, s), 3.94 (2H, s).
MS: 341(M+).

Example 1

To a solution of 447 mg (1 mmole) of 1-(2-hydroxy-2-phenylethyl)-4-[10-(2-tetrahydropyranyloxy)decyl]piperazine, 148 mg (1 mmole) of cinnamic acid and 12 mg (0.1 mmole) of 4-dimethylaminopyridine in anhydrous methylene chloride (7 ml) was added a solution of 309 mg (1.5 mmoles) of N,N'-dicyclohexylcarbodiimide in methylene chloride (3 ml) with ice-cooling, and the mixture was stirred at room temperature for 24 hours. The precipitated crystals were filtered off and washed with methylene chloride. The mother liquor and the washings were concentrated under reduced pressure. The residue was purified by silica gel column chromatography (chloroform:methanol=15:1). The protected product obtained was dissolved in 15 ml of methanol and p-toluenesulfonic acid (3 equivalents) was added thereto. The mixture obtained was refluxed for 2 hours and the solvent was evaporated under reduced pressure. The residue was purified by silica gel column chromatography (chloroform: methanol=10:1) and the resulting oily product was dissolved in ether. A solution of maleic acid (2.1 equivalents) in ether was added and the precipitated crystals were collected by filtration. The crystals were washed with ether thoroughly, giving 520 mg (yield: 69%) of compound 1 listed in No. 1 in Table 2 below.

Melting point 143.5°-144.5° C.

Examples 2 to 39

Compounds 2 to 39 shown below in Table 2 were prepared by following the general procedure of Example 1. Among the elemental analysis data shown in Table 2, those actually found by the analysis are described in the upper position, and theoretical values are described in the lower position.

Example 40

A 223 mg (0.5 mmole) quantity of compound 23 was dissolved in 12 ml of anhydrous methylene chloride. A 0.14 ml (1.0 mmole) quantity of triethylamine and 0.10 ml (1.1 mmoles) of ethyl chlorocarbonate were added dropwise and the mixture was stirred with ice-cooling for 1 hour. The reaction mixture was diluted with 50 ml of methylene chloride and washed with 20 ml of water. The mixture was dried over anhydrous magnesium sulfate and concentrated under reduced pressure. The residue was purified by silica gel column chromatography (chloroform:methanol=10:1) and converted to the corresponding maleate in the same manner as in Example 1, giving 303 mg (yield: 86%) of compound 40 as shown in Table 2.

Melting point 109°-110° C.

Examples 41 to 46

Compounds 41 to 46 shown below in Table 2 were produced by following the general procedure of Example 40. Among the elemental analysis data shown in Table 2, those actually found by the analysis are described in the upper position, and theoretical values are described in the lower position.

Example 47

A 254 mg (0.5 mmole) quantity of compound 24 was dissolved in 7 ml of anhydrous N,N-dimethylformamide. A 260 mg (1.2 mmoles) quantity of N-t-butoxycarbonylvaline and 162 mg (1.2 mmoles) of 1-hydroxybenzotriazol were added. A 247 mg (1.2 mmoles) quantity of N,N'-dicyclohexylcarbodiimide was further added thereto with ice-cooling and the mixture was stirred for 30 minutes. Then the reaction mixture was allowed to gradually warm to room temperature and was stirred for 12 hours. The precipitated crystals were collected by filtration and washed with ethyl acetate. The mother liquor and the washings were combined and the mixture was diluted with 70 ml of ethyl acetate. The collected organic layer was washed with 15 ml of water, dried over anhydrous magnesium sulfate and concentrated under reduced pressure. The residue was purified by silica gel column chromatography (chloroform:methanol=15:1). The obtained oily product was dissolved in 5 ml of ethyl acetate, and 20 ml of 4 N hydrochloric acid-ethyl acetate solution was added to the solution with ice-cooling, and the mixture obtained was stirred for 1 hour. The precipitated crystals were collected by filtration, washed with a small quantity of ether and dried under reduced pressure, giving 285 mg (yield: 62%) of compound 47 as shown below in Table 2

Melting point 186°-190° C.

Examples 48 to 50

Compounds 48 to 50 shown below in Table 2 were prepared by following the general procedure of Example 47. Among the elemental analysis data shown in Table 2, those actually found by the analysis are described in the upper position, and theoretical values are described in the lower position.

Example 51

A 0.2 ml (2.2 mmoles) quantity of n-propylisocyanate was added to a solution of 507 mg (1.0 mmole) of compound 24 in 3 ml of pyridine with ice-cooling, and the mixture was stirred at room temperature for 12 hours. The reaction mixture was diluted with 60 ml of ethyl acetate, washed sequentially with a saturated aqueous copper sulfate solution and a brine and dried over anhydrous magnesium sulfate and concentrated under reduced pressure. The residue was purified by silica gel column chromatography (chloroform:methanol=15:1), followed by drying under reduced pressure, giving 567 mg (yield: 82%) of compound 51.

Melting point 115°-116° C.

Example 52

A 357 mg (1 mmole) quantity of 11-(1-piperazyl)undecanoic acid methyl ester hydrochloride, 180 mg (1 mmole) of caffeic acid, 168 mg (2 mmoles) of sodium hydrogen carbonate, 135 mg (1 mmole) of 1-hydroxybenzotriazol and 206 mg (1 mmole) of N,N'-dicyclohexylcarbodiimide were added to 10 ml of N,N-dimethylformamide and the mixture was stirred at room temperature for 24 hours. The precipitated crystals were filtered off and washed with N,N-dimethylformamide, and the filtrate was concentrated under reduced pressure. The residue was purified by silica gel column chromatography (chloroform:methanol=10:1), giving 253 mg (yield: 56%) of compound 52 as shown in Table 2.

Example 53

A 312 mg (yield: 62%) quantity of compound 53 as shown in Table 2 was prepared in the same manner as in Example 52 using 415 mg (1 mmole) of 1-(2-aminoacetyl)-4-(10-methoxycarbonyldecyl)piperazine hydrochloride, 180 mg (1 mmole) of caffeic acid, 168 mg (2 mmoles) of sodium hydrogen carbonate, 135 mg (1 mmole) of 1-hydroxybenzotriazol and 206 mg (1 mmole) of N,N'-dicyclohexylcarbodiimide.

Table 1 shows the two starting compounds used in Examples 1 to 53. Table 2 shows the structure, melting point, molecular formula and elemental analysis results of compounds 1 to 53 of the invention prepared in Examples 1 to 53.

TABLE 1

| No. | Starting compound (1) | Starting compound (2) |
|---|---|---|
| 1 | HO—CH—CH₂—N(piperazine)N—(CH₂)₁₀—O—(tetrahydropyran), phenyl | Ph—CH=CH—COOH |
| 2 | HO—CH—CH₂—N(piperazine)N—(CH₂)₁₀—O—(tetrahydropyran), phenyl | 3,4-(CH₃O)₂-C₆H₃—CH=CH—COOH |
| 3 | HO—CH—CH₂—N(piperazine)N—(CH₂)₁₀—O—(tetrahydropyran), phenyl | 3-CH₃O-4-HO-C₆H₃—CH=CH—COOH |
| 4 | HO—CH—CH₂—N(piperazine)N—(CH₂)₁₀—O—(tetrahydropyran), phenyl | 3,4-(CH₃OCH₂CH₂OCH₂O)₂-C₆H₃—CH=CH—COOH |
| 5 | HO—CH—CH₂—N(piperazine)N—(CH₂)₁₀—O—(tetrahydropyran), phenyl | 3,4-(HO)₂-C₆H₃—COOH |
| 6 | HO—CH—CH₂—N(piperazine)N—(CH₂)₁₀—O—(tetrahydropyran), phenyl | 3-CH₃O-4-HO-C₆H₃—COOH |
| 7 | HO—CH—CH₂—N(piperazine)N—(CH₂)₁₀—O—(tetrahydropyran), phenyl | 3-Cl-4-HO-C₆H₃—COOH |
| 8 | HO—CH—CH₂—N(piperazine)N—(CH₂)₁₀—O—(tetrahydropyran), phenyl | 3,4-(HO)₂-C₆H₃—CH₂COOH |

TABLE 1-continued

| No. | Starting compound (1) | Starting compound (2) |
|---|---|---|
| 9 | HO–CH–CH₂–N(piperazine)N–(CH₂)₁₀–O–(tetrahydropyran), phenyl | 4-HO-C₆H₄-CH₂CH₂COOH |
| 10 | HO–CH–CH₂–N(piperazine)N–(CH₂)₁₀–O–(tetrahydropyran), phenyl | 3,4-bis(C₆H₅–CH₂–O)–C₆H₃–COOH |
| 11 | HO–CH–CH₂–N(piperazine)N–(CH₂)₁₀–O–(tetrahydropyran), phenyl | 3-(C₆H₅–CH₂–O)–C₆H₄–COOH |
| 12 | HO–CH–CH₂–N(piperazine)N–(CH₂)₁₀–O–(tetrahydropyran), phenyl | 4-(C₆H₅–CH₂–O)–C₆H₄–COOH |
| 13 | HO–CH–CH₂–N(piperazine)N–(CH₂)₁₀–O–(tetrahydropyran), phenyl | 4-(C₆H₅–CH₂–O)–C₆H₄–CH₂CH₂COOH |
| 14 | HO–CH–CH₂–N(piperazine)N–(CH₂)₁₀–O–(tetrahydropyran), phenyl | 3,4-bis(CH₃OCH₂CH₂OCH₂O)–C₆H₃–CH=CH–COOH |
| 15 | HO–CH–CH₂–N(piperazine)N–(CH₂)₁₀–O–(tetrahydropyran), 4-Cl-phenyl | 3,4-bis(CH₃OCH₂CH₂OCH₂O)–C₆H₃–CH=CH–COOH |
| 16 | HO–CH–CH₂–N(piperazine)N–(CH₂)₁₀–O–(tetrahydropyran), 4-Cl-phenyl | 3,4-(HO)₂–C₆H₃–COOH |

TABLE 1-continued

| No. | Starting compound (1) | Starting compound (2) |
|---|---|---|
| 17 | HO–CH–CH$_2$–N(piperazine)N–C$_{10}$H$_{21}$, phenyl with Cl | 3,4-dihydroxybenzoic acid (HO, HO, COOH on benzene) |
| 18 | HO–CH–CH$_2$–N(piperazine)N–(CH$_2$)$_{10}$–O–(tetrahydropyranyl), 3,4-dichlorophenyl | 3,4-dihydroxybenzoic acid |
| 19 | HO–CH–CH$_2$–N(piperazine)N–C$_{10}$H$_{21}$, phenyl | CH$_3$OCH$_2$CH$_2$OCH$_2$O– (×2 at 3,4) –C$_6$H$_3$–CH=CH–COOH |
| 20 | HO–CH–CH$_2$–N(piperazine)N–C$_{10}$H$_{21}$, phenyl | 3,4-dihydroxybenzoic acid |
| 21 | Reference Example 1 | CH$_3$OCH$_2$CH$_2$OCH$_2$O– (×2) –C$_6$H$_3$–CH=CH–COOH |
| 22 | Reference Example 1 | 3,4-dihydroxybenzoic acid |
| 23 | Reference Example 2 | CH$_3$OCH$_2$CH$_2$OCH$_2$O– (×2) –C$_6$H$_3$–CH=CH–COOH |
| 24 | Reference Example 3 | CH$_3$OCH$_2$CH$_2$OCH$_2$O– (×2) –C$_6$H$_3$–CH=CH–COOH |
| 25 | Reference Example 4 | CH$_3$OCH$_2$CH$_2$OCH$_2$O– (×2) –C$_6$H$_3$–CH=CH–COOH |
| 26 | Reference Example 5 | CH$_3$OCH$_2$CH$_2$OCH$_2$O– (×2) –C$_6$H$_3$–CH=CH–COOH |

TABLE 1-continued

| No. | Starting compound (1) | Starting compound (2) |
|---|---|---|
| 27 | Reference Example 3 | 3-methoxy-4-hydroxy-phenyl-CH=CH—COOH (CH$_3$O and HO on benzene ring, CH=CH—COOH substituent) |
| 28 | Reference Example 3 | 3,4-dimethoxyphenyl-CH=CH—COOH (CH$_3$O, CH$_3$O on benzene ring) |
| 29 | Reference Example 3 | 3,4-methylenedioxyphenyl-CH=CH—COOH (O—CH$_2$—O fused on benzene ring) |
| 30 | Reference Example 3 | 3-hydroxy-4-methoxy-phenyl-CH=CH—COOH (HO and CH$_3$O on benzene ring) |
| 31 | Reference Example 3 | 3,4-dihydroxybenzoic acid (HO, HO on benzene ring, COOH substituent) |
| 32 | Reference Example 6 | CH$_3$OCH$_2$CH$_2$OCH$_2$O and CH$_3$OCH$_2$CH$_2$OCH$_2$O on benzene ring, CH=CH—COOH substituent |
| 33 | Reference Example 7 | CH$_3$OCH$_2$CH$_2$OCH$_2$O and CH$_3$OCH$_2$CH$_2$OCH$_2$O on benzene ring, CH=CH—COOH substituent |
| 34 | Reference Example 8 | CH$_3$OCH$_2$CH$_2$OCH$_2$O and CH$_3$OCH$_2$CH$_2$OCH$_2$O on benzene ring, CH=CH—COOH substituent |
| 35 | HN⟨piperazine⟩N—C$_{10}$H$_{21}$ | CH$_3$OCH$_2$CH$_2$OCH$_2$O and CH$_3$OCH$_2$CH$_2$OCH$_2$O on benzene ring, CH=CH—COOH substituent |
| 36 | HN⟨piperazine⟩N—C$_8$H$_{17}$ | CH$_3$OCH$_2$CH$_2$OCH$_2$O and CH$_3$OCH$_2$CH$_2$OCH$_2$O on benzene ring, CH=CH—COOH substituent |
| 37 | HN⟨piperazine⟩N—C$_6$H$_{13}$ | CH$_3$OCH$_2$CH$_2$OCH$_2$O and CH$_3$OCH$_2$CH$_2$OCH$_2$O on benzene ring, CH=CH—COOH substituent |
| 38 | Reference Example 9 | CH$_3$OCH$_2$CH$_2$OCH$_2$O and CH$_3$OCH$_2$CH$_2$OCH$_2$O on benzene ring, CH=CH—COOH substituent |
| 39 | Reference Example 9 | 3,4-dihydroxybenzoic acid (HO, HO on benzene ring, COOH substituent) |
| 40 | Example 23 | Ethyl chlorocarbonate |

TABLE 1-continued

| No. | Starting compound (1) | Starting compound (2) |
|---|---|---|
| 41 | Example 24 | Ethyl chlorocarbonate |
| 42 | Example 27 | Ethyl chlorocarbonate |
| 43 | Example 32 | Ethyl chlorocarbonate |
| 44 | Example 21 | Ethyl chlorocarbonate |
| 45 | Example 24 | Isobutyryl chloride |
| 46 | Example 24 | Diethylchlorophosphate |
| 47 | Example 24 | N-t-butoxycarbonylvaline |
| 48 | Example 27 | N-t-butoxycarbonylvaline |
| 49 | Example 30 | N-t-butoxycarbonylvaline |
| 50 | Example 24 | N-acetylvaline |
| 51 | Example 24 | n-Propylisocyanate |
| 52 | Reference Example 10 | 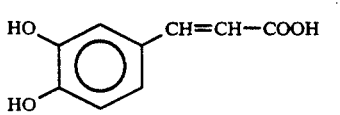 |
| 53 | Reference Example 11 | 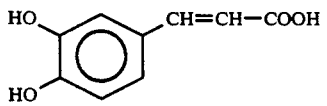 |

TABLE 2

| No | Structural formula | m.p. (°C.) | Molecular formula | Results of elemental analysis | | |
|----|-------------------|------------|-------------------|------|------|------|
|    |                   |            |                   | C    | H    | N    |
| 1  | Piperazine derivative with N(CH₂)₁₀OH, cinnamate ester of 2-phenyl-2-hydroxyethyl group · 9/4 CHCOOH‖CHCOOH | 143.5~144.5 | $C_{31}H_{44}N_2O_3 \cdot 9/4 C_4H_4O_4$ | 59.17<br>59.35 | 6.95<br>7.00 | 3.56<br>3.70 |
| 2  | Piperazine derivative with N(CH₂)₁₀OH, 3,4-dimethoxycinnamate ester of 2-phenyl-2-hydroxyethyl group · 9/4 CHCOOH‖CHCOOH | 135~137.5 | $C_{33}H_{48}N_2O_5 \cdot 9/4 C_4H_4O_4$ | 61.86<br>61.98 | 7.30<br>7.06 | 3.46<br>3.44 |
| 3  | Piperazine derivative with N(CH₂)₁₀OH, 3-methoxy-4-hydroxycinnamate ester of 2-phenyl-2-hydroxyethyl group · 9/4 CHCOOH‖CHCOOH | 119~121 | $C_{32}H_{46}N_2O_5 \cdot 9/4 C_4H_4O_4$ | 61.29<br>61.56 | 6.69<br>6.93 | 3.05<br>3.50 |

TABLE 2-continued

| No | Structural formula | m.p. (°C.) | Molecular formula | Results of elemental analysis |||
|---|---|---|---|---|---|---|
| | | | | C | H | N |
| 4 | [structure: caffeic acid ester of 2-phenyl-2-(azepan-1-yl-methyl... with N(CH$_2$)$_{10}$OH, 9/4 CHCOOH / CHCOOH] | 86~89 | C$_{31}$H$_{44}$N$_2$O$_5$·9/4C$_4$H$_4$O$_4$ | 60.99<br>61.14 | 7.23<br>6.80 | 3.62<br>3.56 |
| 5 | [structure with N(CH$_2$)$_{10}$OH, 2 CHCOOH / CHCOOH · H$_2$O] | 105~107.5 | C$_{29}$H$_{42}$N$_2$O$_6$·2C$_4$H$_4$O$_4$·H$_2$O | 59.17<br>59.35 | 6.95<br>7.00 | 3.56<br>3.70 |
| 6 | [structure with H$_3$CO, HO on ring, N(CH$_2$)$_{10}$OH] | 114~116 | C$_{30}$H$_{44}$N$_2$O$_5$ | 70.16<br>70.28 | 8.85<br>8.65 | 5.53<br>5.46 |
| 7 | [structure with Cl, HO on ring, N(CH$_2$)$_{10}$OH, 2 CHCOOH / CHCOOH] | 127.5~129 | C$_{29}$H$_{41}$N$_2$O$_4$Cl·2C$_4$H$_4$O$_4$ | 59.32<br>59.31 | 6.82<br>6.57 | 3.85<br>3.74 |

TABLE 2-continued

| No | Structural formula | m.p. (°C.) | Molecular formula | Results of elemental analysis | | |
|---|---|---|---|---|---|---|
| | | | | C | H | N |
| 8 | [structure: 3,4-dihydroxyphenyl-CH₂-COO-CH(C₆H₅)-CH₂-N(piperazine)-(CH₂)₁₀OH] · 2 CHCOOH=CHCOOH · H₂O | 103~104 | $C_{30}H_{44}N_2O_5 \cdot 2C_4H_4O_4 \cdot H_2O$ | 60.04 59.93 | 7.04 7.14 | 3.77 3.67 |
| 9 | [structure: 4-hydroxyphenyl-CH₂CH₂-COO-CH(C₆H₅)-CH₂-N(piperazine)-(CH₂)₁₀OH] · 9/4 CHCOOH=CHCOOH | 140.5~143.5 | $C_{31}H_{46}N_2O_4 \cdot 9/4 C_4H_4O_4$ | 61.94 62.24 | 7.58 7.18 | 3.29 3.63 |
| 10 | [structure: 3,4-bis(benzyloxy)phenyl-COO-CH(C₆H₅)-CH₂-N(piperazine)-(CH₂)₁₀OH] · 2 CHCOOH=CHCOOH | 137~139.5 | $C_{43}H_{54}N_2O_5 \cdot 2C_4H_4O_4$ | 67.09 67.24 | 7.03 6.86 | 3.07 3.08 |

TABLE 2-continued

| No | Structural formula | m.p. (°C.) | Molecular formula | Results of elemental analysis C | H | N |
|----|---|---|---|---|---|---|
| 11 | H₅C₆CH₂O—C₆H₄—COO—CH(C₆H₅)—CH₂—N(piperidine)—N(CH₂)₁₀OH · 2 CHCOOH/CHCOOH | 142~145 | C₃₆H₄₈N₂O₄·2C₄H₄O₄ | 65.22 / 65.66 | 7.27 / 7.01 | 3.39 / 3.48 |
| 12 | H₅C₆CH₂O—C₆H₄—COO—CH(C₆H₅)—CH₂—N(piperidine)—N(CH₂)₁₀OH | 93.5~94.5 | C₃₆H₄₈N₂O₄ | 75.33 / 75.49 | 8.51 / 8.45 | 4.81 / 4.89 |
| 13 | H₅C₆CH₂O—C₆H₄—CH₂CH₂—COO—CH(C₆H₅)—CH₂—N(piperidine)—N(CH₂)₁₀OH · 2 CHCOOH/CHCOOH | 159~161 | C₃₈H₅₂N₂O₄·2C₄H₄O₄ | 65.29 / 65.49 | 7.21 / 7.13 | 3.24 / 3.25 |
| 14 | (HO)₂C₆H₃—CH=CH—COO—CH(C₆H₅)—CH₂—N(piperidine)—N(CH₂)₆OH · 2 CHCOOH/CHCOOH · ½H₂O | 130~133 | C₂₇H₃₆N₂O₅·2C₄H₄O₄·½H₂O | 59.21 / 59.23 | 6.30 / 6.33 | 4.04 / 3.95 |

TABLE 2-continued

| No | Structural formula | m.p. (°C.) | Molecular formula | Results of elemental analysis | | |
|---|---|---|---|---|---|---|
| | | | | C | H | N |
| 15 | [structure: 4-chlorophenyl with N(CH₂)₁₀OH piperazine, cinnamate ester with 3,4-dihydroxyphenyl] · 2 CHCOOH ‖ CHCOOH · ½H₂O | 92~94 | C₃₁H₄₃N₂O₅Cl·2C₄H₄O₄·½H₂O | 58.56<br>58.53 | 6.49<br>6.68 | 3.50<br>3.50 |
| 16 | [structure: 4-chlorophenyl with N(CH₂)₁₀OH piperazine, 3,4-dihydroxybenzoate ester] · ½H₂O | 137~139.5 | C₂₉H₄₁N₂O₅Cl·½H₂O | 64.23<br>64.25 | 7.85<br>7.81 | 5.14<br>5.17 |
| 17 | [structure: 4-chlorophenyl with NC₁₀H₂₁ piperazine, 3,4-dihydroxybenzoate ester] | 178~179 | C₂₉H₄₁N₂O₄Cl | 67.13<br>67.36 | 8.23<br>7.99 | 5.32<br>5.41 |

TABLE 2-continued

| No | Structural formula | m.p. (°C.) | Molecular formula | Results of elemental analysis | | |
|---|---|---|---|---|---|---|
| | | | | C | H | N |
| 18 | [structure: 3,4-dihydroxyphenyl-CH(COO-)-CH2-piperazine-N(CH2)10OH with 3,4-Cl2-phenyl] | 114~116 | C29H40N2O5Cl2·2C4H4O4 | 55.37<br>55.57 | 6.22<br>6.05 | 3.38<br>3.50 |
| 19 | [structure: cinnamate ester with piperazine-NC10H21, 2CHCOOH/CHCOOH·H2O] | 103~105 | C31H44N2O4·2C4H4O4·H2O | 61.74<br>61.73 | 6.86<br>7.17 | 3.70<br>3.69 |
| 20 | [structure: phenyl-CH(COO-)-CH2-piperazine-NC10H21] | 142~144 | C29H42N2O4 | 71.84<br>71.72 | 8.45<br>8.77 | 5.73<br>5.80 |
| 21 | [structure: CONH-CH(phenyl)-C(O)-piperazine-NC10H21 ·½H2O] | 76~79.5 | C31H43N3O4·½H2O | 70.12<br>70.16 | 8.39<br>8.36 | 7.79<br>7.92 |

TABLE 2-continued

| No | Structural formula | m.p. (°C.) | Molecular formula | Results of elemental analysis C | H | N |
|---|---|---|---|---|---|---|
| 22 | HO-, HO- substituted phenyl-CH(CONH-)-C(=O)-N(homopiperazine)-NC$_{10}$H$_{21}$ ; CHCOOH=CHCOOH · 5/6H$_2$O | 80~85 | C$_{29}$H$_{41}$N$_3$O$_4$·C$_4$H$_4$O$_4$·5/6H$_2$O | 63.59 / 63.24 | 8.03 / 7.51 | 6.74 / 6.70 |
| 23 | HO-, HO- substituted phenyl-CH=CH-CONH-CH$_2$-C(=O)-N(homopiperazine)-NC$_{10}$H$_{21}$ · ¼H$_2$O | 178~181 | C$_{25}$H$_{39}$N$_3$O$_4$·¼H$_2$O | 66.71 / 66.62 | 8.85 / 8.81 | 9.34 / 8.97 |
| 24 | HO-, HO- substituted phenyl-CH=CH-CONH-CH(phenyl)-CH$_2$-N(homopiperazine)-NC$_{10}$H$_{21}$ · ¼H$_2$O | 98~100.5 | C$_{31}$H$_{45}$N$_3$O$_3$·¼H$_2$O | 71.66 / 72.06 | 8.93 / 8.97 | 7.80 / 8.13 |
| 25 | HO-, HO- substituted phenyl-CH=CH-CONH-CH(phenyl)-CH$_2$-N(homopiperazine)-NC$_{12}$H$_{25}$ · ¼H$_2$O | 86~88 | C$_{33}$H$_{49}$N$_3$O$_3$·¼H$_2$O | 72.18 / 72.16 | 9.33 / 9.27 | 7.43 / 7.65 |

TABLE 2-continued

| No | Structural formula | m.p. (°C.) | Molecular formula | Results of elemental analysis C | H | N |
|---|---|---|---|---|---|---|
| 26 | HO-C6H3(OH)-CH=CH-CONH-CH(Ph)-CH2-N(piperidine)-NC15H31 | 90~92 | $C_{36}H_{55}N_3O_3 \cdot \frac{1}{4}H_2O$ | 73.47 / 73.68 | 9.85 / 9.62 | 7.05 / 7.16 |
| 27 | H3CO-C6H3(OH)-CH=CH-CONH-CH(Ph)-CH2-N(piperidine)-NC10H21 · 2 CHCOOH‖CHCOOH · ½H2O | 123~125 | $C_{32}H_{47}N_3O_3 \cdot 2C_4H_4O_4 \cdot \frac{1}{2}H_2O$ | 63.32 / 63.73 | 7.36 / 7.35 | 5.19 / 5.57 |
| 28 | H3CO-C6H3(OCH3)-CH=CH-CONH-CH(Ph)-CH2-N(piperidine)-NC10H21 · 2 CHCOOH‖CHCOOH · ½H2O | 144~146 | $C_{33}H_{49}N_3O_3 \cdot 2C_4H_4O_4 \cdot \frac{1}{2}H_2O$ | 63.63 / 63.63 | 7.59 / 7.51 | 5.40 / 5.43 |
| 29 | (methylenedioxyphenyl)-CH=CH-CONH-CH(Ph)-CH2-N(piperidine)-NC10H21 · 2 CHCOOH‖CHCOOH | 152~154 | $C_{32}H_{45}N_3O_3 \cdot 2C_4H_4O_4$ | 63.65 / 63.89 | 7.33 / 7.11 | 5.67 / 5.59 |

TABLE 2-continued

| No | Structural formula | m.p. (°C.) | Molecular formula | Results of elemental analysis | | |
|---|---|---|---|---|---|---|
| | | | | C | H | N |
| 30 | HO, H₃CO-phenyl-CH=CH-CONH-CH(C₆H₅)-CH₂-N(piperidine)-NC₁₀H₂₁ · ½H₂O | 60~62 | C₃₂H₄₇N₃O₃·½H₂O | 72.42<br>72.42 | 9.14<br>9.12 | 7.82<br>7.92 |
| 31 | HO, HO-phenyl-CH=CH-CONH-CH(C₆H₅)-CH₂-N(piperidine)-NC₁₀H₂₁ · 2 CHCOOH/CHCOOH · H₂O | 131~134 | C₂₉H₄₃N₃O₃·2C₄H₄O₄·½H₂O | 61.36<br>61.48 | 7.35<br>7.25 | 5.69<br>5.81 |
| 32 | HO, HO-phenyl-CH=CH-CONH-CH₂-CH₂-N(piperidine)-NC₁₀H₂₁ · 2 CHCOOH/CHCOOH · H₂O | 193~197 | C₂₅H₄₁N₃O₃·2C₄H₄O₄·H₂O | 58.13<br>58.14 | 7.44<br>7.54 | 6.13<br>6.14 |
| 33 | HO, HO-phenyl-CH=CH-CONH-CH(C₆H₅)-CH₂-N(piperidine)-NC₈H₁₇ · 3/2H₂O | 101~104 | C₂₉H₄₁N₃O₃·3/2H₂O | 69.09<br>68.74 | 8.30<br>8.75 | 8.28<br>8.29 |

TABLE 2-continued

| No | Structural formula | m.p. (°C.) | Molecular formula | Results of elemental analysis C | H | N |
|---|---|---|---|---|---|---|
| 34 | [3,4-dihydroxyphenyl-CH=CH-CONH-CH(phenyl)-CH2-piperazine-NC6H13] ·H2O | 114~118 | C27H37N3O3·H2O | 69.37<br>69.05 | 8.72<br>8.37 | 8.52<br>8.95 |
| 35 | [3,4-dihydroxyphenyl-CH=CH-CON-piperidine-NC10H21] | 170~172 | C23H36N2O3 | 70.85<br>71.10 | 9.65<br>9.34 | 7.10<br>7.21 |
| 36 | [3,4-dihydroxyphenyl-CH=CH-CON-piperidine-NC8H17] | 172~173 | C21H32N2O3 | 69.79<br>69.97 | 7.03<br>8.95 | 7.61<br>7.77 |
| 37 | [3,4-dihydroxyphenyl-CH=CH-CON-piperidine-NC6H13] ·1/7H2O | 175~177 | C19H28N2O3·1/7H2O | 68.10<br>68.12 | 8.74<br>8.51 | 8.18<br>8.36 |
| 38 | [3,4-dihydroxyphenyl-CH=CH-CONH-CH(phenyl)-CH2-piperazine-N(CH2)10OH] | 165~167 | C31H45N3O4 | 71.09<br>71.10 | 8.79<br>8.66 | 8.01<br>8.02 |

TABLE 2-continued

| No | Structural formula | m.p. (°C.) | Molecular formula | Results of elemental analysis C | H | N |
|---|---|---|---|---|---|---|
| 39 | [structure: dihydroxyphenyl-CONH-CH(phenyl)-CH2-N(piperazine)-N(CH2)10OH · 2 CHCOOH=CHCOOH · ½H2O] | 106~108 | $C_{29}H_{43}N_3O_4 \cdot 2C_4H_4O_4 \cdot \tfrac{1}{2}H_2O$ | 60.09 60.15 | 7.67 7.69 | 5.48 5.67 |
| 40 | [structure: diethoxycarbonyloxyphenyl-CH=CH-CONH-CH2-piperazine-NC10H21 · CHCOOH=CHCOOH] | 109~110 | $C_{31}H_{47}N_3O_3 \cdot C_4H_4O_4$ | 59.40 59.56 | 7.27 7.28 | 5.73 5.95 |
| 41 | [structure: diethoxycarbonyloxyphenyl-CH=CH-CONH-CH(phenyl)-CH2-piperazine-NC10H21 · 2 CHCOOH=CHCOOH] | 130~132 | $C_{37}H_{53}N_3O_7 \cdot 2C_4H_4O_4$ | 60.72 61.14 | 7.12 6.96 | 4.83 4.75 |
| 42 | [structure: methoxy-ethoxycarbonyloxyphenyl-CH=CH-CONH-CH(phenyl)-CH2-piperazine-NC10H21 · 2 CHCOOH=CHCOOH] | 141~143 | $C_{35}H_{51}N_3O_5 \cdot 2C_4H_4O_4$ | 61.32 62.53 | 7.28 7.20 | 4.89 5.09 |

TABLE 2-continued

| No | Structural formula | m.p. (°C.) | Molecular formula | Results of elemental analysis | | |
|----|---|---|---|---|---|---|
| | | | | C | H | N |
| 43 | [structure with H5C2OCO groups, CONH, NC10H21, 2 CHCOOH/CHCOOH·H2O] | 163-165 | C31H49N3O7·2C4H4O4·H2O | 56.41<br>56.71 | 7.16<br>7.20 | 4.98<br>5.09 |
| 44 | [structure with H5C2OCO groups, CON with phenyl, NC10H21, CHCOOH/CHCOOH·H2O] | 65~68 | C37H51N3O3·C4H4O4·H2O | 61.34<br>61.56 | 7.16<br>7.18 | 4.97<br>5.25 |
| 45 | [structure with (H3C)2CHCO groups, CONH-CH(phenyl)-CH2-N piperazine-NC10H21, 2 CHCOOH/CHCOOH] | 118~119 | C39H57N3O5·2C4H4O4 | 63.94<br>64.14 | 7.64<br>7.45 | 4.97<br>4.78 |
| 46 | [structure with (H5C2O)2PO groups, CONH-CH(phenyl)-CH2-N piperazine-NC10H21, 2 CHCOOH/CHCOOH·H2O] | 98~99 | C39H63N3O9P2·2C4H4O4·H2O | 54.38<br>54.75 | 7.23<br>7.14 | 3.76<br>4.08 |

TABLE 2-continued

| No | Structural formula | m.p. (°C.) | Molecular formula | Results of elemental analysis C | H | N |
|---|---|---|---|---|---|---|
| 47 | (structure) 4HCl.4H₂O | 186~190 | $C_{41}H_{63}N_5O_5 \cdot 4HCl \cdot 4H_2O$ | 53.17<br>53.30 | 7.79<br>8.18 | 7.34<br>7.58 |
| 48 | (structure) .5/2HCl.H₂O | 165~170 | $C_{37}H_{56}N_4O_4 \cdot 5/2HCl \cdot H_2O$ | 60.87<br>60.86 | 8.35<br>8.14 | 7.67<br>7.67 |
| 49 | (structure) .5/2HCl.H₂O | 165~168 | $C_{37}H_{56}N_4O_4 \cdot 5/2HCl \cdot H_2O$ | 60.87<br>60.86 | 8.35<br>8.14 | 7.67<br>7.67 |
| 50 | (structure) | 70~73 | $C_{45}H_{70}N_5O_7$ | 66.15<br>66.17 | 8.65<br>8.64 | 8.57<br>8.41 |

TABLE 2-continued

| No | Structural formula | m.p. (°C.) | Molecular formula | Results of elemental analysis C | H | N |
|---|---|---|---|---|---|---|
| 51 | [structure with H$_7$C$_3$HNCO groups on benzene, CONH, phenyl, NC$_{10}$H$_{21}$ piperidine] | 115~116 | C$_{39}$H$_{59}$N$_5$O$_5$·½H$_2$O | 67.79 67.75 | 9.09 8.82 | 10.47 10.13 |
| 52 | [structure with HO, HO on benzene, CON-piperidine-NC$_{10}$H$_{20}$CO$_2$CH$_3$] ½H$_2$O | 156~158 | C$_{25}$H$_{38}$N$_2$O$_5$·½H$_2$O | 66.39 66.35 | 8.76 8.61 | 6.25 6.19 |
| 53 | [structure with HO, HO on benzene, CONH-CH$_2$-CO-piperidine-NC$_{10}$H$_{20}$CO$_2$CH$_3$] | 148~150 | C$_{27}$H$_{41}$N$_3$O$_6$ | 63.99 64.30 | 8.10 8.21 | 8.29 8.34 |

Pharmacological tests

(1) Cyclooxygenase inhibitory effect

The assay was carried out by the method described in Biochem. Pharmacol. 25, 2479-2484 (1976).

$^{14}$C-Arachidonic acid was reacted with seminal vesicular gland microsomes and the test drugs at various concentrations over a predetermined period of time and the obtained prostaglandin $E_2$ was separated by thin-layer chromatography. The radioactivity was determined by liquid scintillation counter. The $IC_{50}$ values were calculated by the comparison with the radioactivity of the control.

2) 5-Lipoxygenase inhibitory effect

The assay was carried out by the method described in Journal of Biological Chemistry 258, 5754-5758 (1983) Casein was injected into the abdominal cavity of a guinea pig, and the polymorphonuclear leukocytes were collected and the cytosol fraction was obtained as an enzyme source. $^{14}$C-Arachidonic acid was reacted with the enzyme and the test drugs at various concentrations over a predetermined period of time. The obtained 5-hydroxyeicosatetraenoic acid was separated by thin-layer chromatography and the radioactivity was determined. By the comparison with the radioactivity of the control, the $IC_{50}$ values were calculated.

Table 3 shows the results of the above tests (1) and (2).

TABLE 3

| Compound No. | $IC_{50}$ (μM) Cyclooxygenase inhibitory effect | 5-Lipoxygenase inhibitory effect |
|---|---|---|
| 8 | 9.9 | 0.32 |
| 15 | 3.4 | 0.09 |
| 19 | 4.3 | 0.08 |
| 23 | 4.2 | 0.04 |
| 35 | 8.4 | 0.04 |
| 36 | 2.9 | 0.12 |

3. Effect on allergic asthma

To a guinea pig (Hartley, 350 to 400 g, male) was administered 0.5 ml/kg of a guinea pig anti-ovalbumin IgE serum for passive sensitization. Two days later, the guinea pig was anesthetized with pentobarbital (70 mg/kg) and a cannula and a catheter were each inserted into the trachea and a carotid artery, respectively. Further, the spontaneous respiration of the guinea pig was stopped with use of 0.5 mg/kg of pancuronium bromide and artificial respiration was conducted (100% oxygen at 1 kgf/cm$^2$, respirator: EVM-50A (manufactured by AIKA Co., Ltd.), predetermined flow rate of oxygen: 0.45 l/min, number of respiration: 40 times/min, time for inspiration: 0.25 sec/respiration). The measurement for contraction of respiratory tract was carried out by modified Konzett and Rössler method. A 100 mg quantity of the compound of the present invention was suspended in 5 ml of a 5% Tween-80-phosphate buffered physiological saline solution (pH 6.8). Two hours before the challenge, the test drug was orally administered in a volume of 5 ml/kg. The same quantity of the solvent alone was orally administered to a control group. Further, 2.5 mg/kg of diphenhydramine, 0.05 mg/kg of propranolol and 5 mg/kg of indomethacin were intravenously administered 5 minutes before the challenge. A 22.5 to 35 μg/kg quantity of ovalbumin was intravenously administered and the contraction of respiratory tract was measured as airway resistance with use of a pressure transducer. The maximum airway resistance was taken as 100%, and the change in the airway resistance caused a predetermined period of time after the challenge was shown as the ratio relative to the maximum airway resistance. Table 4 shows the test results.

TABLE 4

| Compound No. | Airway resistance (%, mean ± standard error) Time (minutes) | | |
|---|---|---|---|
| | 3 | 8 | 16 |
| 40 | 22.6 ± 3.7 | 45.6 ± 11.0 | 40.9 ± 11.3 |
| Control | 41.9 ± 7.0 | 79.5 ± 5.4 | 75.3 ± 5.8 |

Given below are Preparation Examples using the compounds of the present invention.

Preparation Example 1. Tablets

Tablets having the following formulation were prepared by the conventional procedure.

| | |
|---|---|
| Compound 15 | 100 mg |
| Lactose | 47 mg |
| Corn starch | 50 mg |
| Crystalline cellulose | 50 mg |
| Hydroxypropyl cellulose | 15 mg |
| Talc | 2 mg |
| Magnesium stearate | 2 mg |
| Ethyl cellulose | 30 mg |
| Unsaturated fatty acid glyceride | 2 mg |
| Titanium dioxide | 2 mg |
| Per tablet | 300 mg |

Preparation Example 2, Granules

Granules having the following formulation were prepared by the conventional procedure.

| | |
|---|---|
| Compound 19 | 200 mg |
| Mannitol | 540 mg |
| Corn starch | 100 mg |
| Crystalline cellulose | 100 mg |
| Hydroxypropyl cellulose | 50 mg |
| Talc | 10 mg |
| Per wrapper | 1000 mg |

Preparation Example 3. Fine granules

Fine granules having the following formulation were prepared by the conventional procedure.

| | |
|---|---|
| Compound 23 | 200 mg |
| Mannitol | 520 mg |
| Corn starch | 100 mg |
| Crystalline cellulose | 100 mg |
| Hydroxypropyl cellulose | 70 mg |
| Talc | 10 mg |
| Per wrapper | 1000 mg |

Preparation Example 4, Capsules

Capsules having the following formulation were prepared by the conventional procedure.

| | |
|---|---|
| Compound 8 | 100 mg |
| Lactose | 50 mg |
| Corn starch | 47 mg |
| Crystalline cellulose | 50 mg |
| Talc | 2 mg |
| Magnesium stearate | 1 mg |
| Per capsule | 250 mg |

Preparation Example 5, Syrups

Syrups having the following formulation were prepared by the conventional procedure.

| | |
|---|---|
| Compound 35 | 1 g |
| Purified sucrose | 60 g |
| Ethyl parahydroxy benzoate | 5 mg |
| Butyl parahydroxy benzoate | 5 mg |
| Flavor | suitable amount |
| Coloring agent | suitable amount |
| Purified water | suitable amount |
| Total amount | 100 ml |

Preparation Example 6, Injections

Injections having the following formulation were produced by the conventional procedure.

| | |
|---|---|
| Compound 36 | 100 mg |
| Distilled water for injections | q.s. |
| Per ampoule | 2 ml |

Preparation Example 7. Suppositories

Suppositories having the following formulation were prepared by the conventional procedure.

| | |
|---|---|
| Compound 15 | 100 mg |
| Witepsol S-55 | 1400 mg |
| (a mixture of mono-, di- and tri-glycerides of saturated fatty acid ranging from lauric acid to stearic acid, product of Dynamite Novel Co.) | |
| Per suppository | 1500 mg |

We claim:

1. A piperazine compound represented by the formula

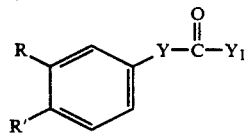

wherein R and R' are the same or different and each represents a hydroxy group, a lower alkoxy group, a halogen atom, a hydrogen atom, a di(lower alkyl) hydrogenphosphate residue or a group —OR" (wherein R" is an aralkyl hydrocarbon group, a lower alkoxycarbonyl group, an amino acid residue, a lower alkylcarbonyl group or a lower alkylcarbamoyl group), or R and R' taken together form a methylenedioxy group, Y is —CH=CH— or —(CH$_2$)$_m$— (wherein m is 0, 1 or 2), and Y$_1$ is a group represented by the formula (2)

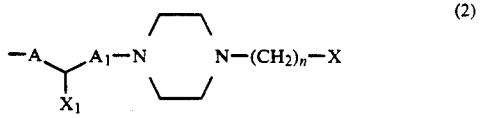

(wherein A is —NH— or —O—, A$_1$ is a methylene group or a carbonyl group, n is 6 to 20, X is a hydroxy group, a hydrogen atom or a lower alkoxycarbonyl group, and X$_1$ is a phenyl group which may be substituted with a halogen atom or a hydrogen atom), or a group represented by the formula (3)

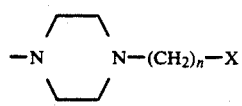

(wherein X and n are as defined above), provided that when Y is the group of the formula (3), each of R and R' is a hydroxy group; or a pharmaceutically acceptable salt thereof.

2. A piperazine compound or a pharmaceutically acceptable salt thereof according to claim 1 wherein R and R' are the same or different and each represents a hydroxy group, a lower alkoxy group, a hydrogen atom, a di(lower alkyl) hydrogenphosphate residue or a group —OR" (wherein R" is a lower alkoxycarbonyl group or an amino acid residue).

3. A piperazine compound or a pharmaceutically acceptable salt thereof according to claim 1 wherein R and R' are the same or different and each represents a hydroxy group, a lower alkoxy group or a group —OR" (wherein R" is a lower alkoxycarbonyl group).

4. A piperazine compound or a pharmaceutically acceptable salt thereof according to claim 1 or 2 wherein Y is —CH=CH—.

5. A piperazine compound or a pharmaceutically acceptable salt thereof according to claim 1 wherein Y$_1$ is the group of the formula (2).

6. A piperazine compound or a pharmaceutically acceptable salt thereof according to claim 1 wherein Y$_1$ is the group of the formula (2) wherein A is —NH—, A$_1$ is a methylene group or a carbonyl group, n is 6 to 15, X is a hydroxy group or a hydrogen atom and X$_1$ is a phenyl group or a hydrogen atom.

7. A piperazine compound or a pharmaceutically acceptable salt thereof according to claim 1 wherein Y$_1$ is the group of the formula (2) wherein A is —NH—, A$_1$ is a methylene group or a carbonyl group, n is 8 to 12, X is a hydrogen atom and X$_1$ is a phenyl group or a hydrogen atom.

8. A piperazine compound or a pharmaceutically acceptable salt thereof according to claim 1 wherein R and R' are the same or different and each represents a hydroxy group, a lower alkoxy group, a hydrogen atom, a di(lower alkyl) hydrogenphosphate residue or a group of —OR" (wherein R" is a lower alkoxycarbonyl group or an amino acid residue), Y is —CH=CH— and Y$_1$ is a group of the formula (2) wherein A is —NH—, A$_1$ is a methylene group or a carbonyl group, n is 6 to 15, X is a hydroxy group or a hydrogen atom and X$_1$ is a phenyl group or a hydrogen atom.

9. A piperazine compound or a pharmaceutically acceptable salt thereof according to claim 1 wherein R and R' are the same or different and each represents a hydroxy group, a lower alkoxy group, or a group —OR" (wherein R" is a lower alkoxycarbonyl group), Y is —CH=CH— and Y$_1$ is the group of the formula (2) wherein A is —NH—, A$_1$ is a methylene group or a carbonyl group, n is 8 to 12, X is a hydrogen atom and X$_1$ is a phenyl group or a hydrogen atom.

10. A composition comprising: a lipoxygenase inhibitory amount of the piperazine compound as claimed in claim 1 or a pharmaceutically acceptable salt thereof; and a pharmaceutically acceptable carrier.

11. A composition as claimed in claim 10 wherein said lipoxygenase is 5-lipoxygenase.

12. A composition as claimed in claim 10 wherein said lipoxygenase is cyclooxygenase.

13. A composition comprising: an anti-asthmatic effective amount of the piperazine compound as claimed in claim 1 or a pharmaceutically acceptable salt thereof; and a pharmaceutically acceptable carrier therefore.

14. A composition comprising: an anti-allergic effective amount of the piperazine compound as claimed in claim 1 or the pharmaceutically acceptable salt thereof and pharmaceutically acceptable carrier therefore.

15. A pharmaceutical composition comprising: a dermatosis treating effective amount of the piperazine compound as claimed in claim 1 or a pharmaceutically acceptable salt thereof; and a pharmaceutically acceptable carrier therefore.

16. A method of inhibiting lipoxygenase which comprises administering to a patient an effective amount of the piperazine compound or the pharmaceutically acceptable salt thereof as defined in claim 1.

17. A method of inhibiting 5-lipoxygenase which comprises administering to a patient an effective amount of the piperazine compound or the pharmaceutically acceptable salt thereof as defined in claim 1.

18. A method of inhibiting cyclooxygenase which comprises administering to a patient an effective amount of the piperazine compound or the pharmaceutically acceptable salt thereof as defined in claim 1.

19. A method of treating allergic asthma which comprises administering to a patient an effective amount of the piperazine compound or the pharmaceutically acceptable salt thereof as defined in claim 1.

20. A process for preparing the piperazine compound as defined in claim 1, the process being characterized in that:

a) for preparing a compound represented by the formula

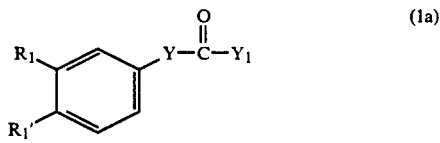

wherein Y and $Y_1$ are as defined in claim 1, and $R_1$ and $R_1'$ are the same or different and each represents a hydroxy group, a lower alkoxy group, an aralkyloxy group, a halogen atom or a hydrogen atom, or $R_1$ and $R_1'$ taken together form a methylenedioxy group, a compound represented by the formula

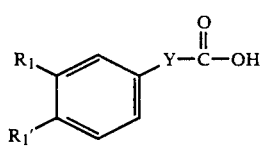

wherein $R_1$, $R_1'$ and Y are as defined above is reacted with a compound represented by the formula

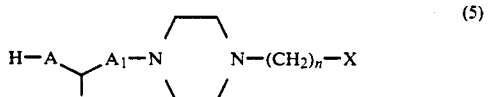

or

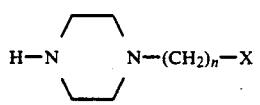

wherein A, $A_1$, X, $X_1$ and n are as defined in claim 1 in a solvent in the presence of a condensing agent and a base, or b) for preparing a compound represented by the formula

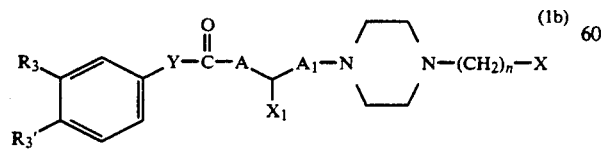

wherein Y, A, $A_1$, X, $X_1$ and n are as defined above, and $R_3$ and $R_3'$ are the same or different and each represents a lower alkoxy group, a halogen atom, a hydrogen atom or a group $-OR_3''$ (wherein $R_3''$ is a lower alkylcarbonyl group or an amino acid residue) with the proviso that at least one of $R_3$ and $R_3'$ is (are) said $-OR_3''$ group, a compound represented by the formula

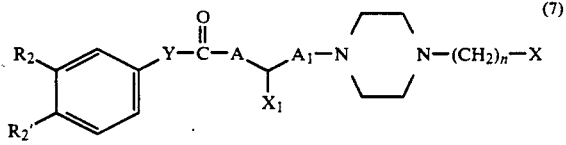

wherein Y, A, $A_1$, X, $X_1$ and n are as defined above, $R_2$ and $R_2'$ are the same or different and each represents a hydroxy group, a lower alkoxy group, a halogen atom or a hydrogen atom with the proviso that at least one of $R_2$ and $R_2'$ is (are) a hydroxy group is reacted with a lower fatty acid or an acid chloride thereof, or an amino acid or an N-protected amino acid in a suitable solvent in the presence of a condensing agent, and when said N-protected amino acid is used, removing the protective group from the obtained compound when required, or c) for preparing a compound represented by the formula

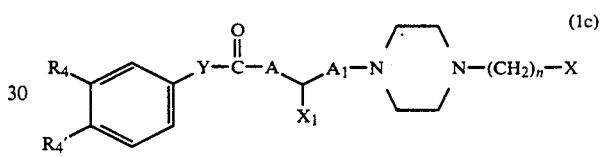

wherein Y, A, $A_1$, X, X and n are as defined above, $R_4$ and $R_4'$ are the same or different and each represents a lower alkoxy group, a halogen atom, a hydrogen atom, a di(lower alkyl) hydrogenphosphate residue or a group $-OR_4''$ (wherein $R_4''$ is a lower alkylcarbamoyl group or a lower alkoxycarbonyl group), with the proviso that at least one of $R_4$ and $R_4'$ is (are) a di(lower alkyl) hydrogenphosphate residue or a group $-OR_4''$, a compound represented by the formula

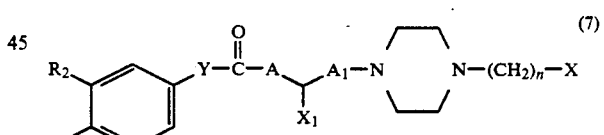

wherein Y, A, $A_1$, X, $X_1$, and n are as defined above, and $R_2$ and $R_2'$ are the same or different and each represents a hydroxy group, a lower alkoxy group, a halogen atom or hydrogen atom with the proviso that at least one of $R_2$ and $R_2'$ is (are) a hydroxy group is reacted with a lower alkyl isocyanate, a di(lower alkyl) chlorophosphate or a lower alkoxycarbonyl chloride in a suitable solvent in the presence of a base, or d) for preparing a compound of the formula (1c) wherein $R_4''$ is a lower alkylcarbamoyl group or a lower alkoxycarbonyl group, said compound of the formula (7) is reacted with phosgene or N,N'-carbonyldiimidazole in a suitable solvent and the resulting reaction product is then reacted with a mono or di(lower alkyl) amine or a lower alcohol in the presence of a base if required.

* * * * *